United States Patent [19]

Newman et al.

[11] Patent Number: 5,003,120

[45] Date of Patent: Mar. 26, 1991

[54] PROCESS FOR SELECTIVE MANUFACTURE OF 2,6-DIISOPROPYLNAPHTHALENES WITH EQUILIBRATION REACTOR

[75] Inventors: Stanley F. Newman, Walnut Creek; Jere D. Fellmann, Livermore; Peter H. Kilner, Sunnyvale, all of Calif.

[73] Assignee: Catalytica, Inc., Mountain View, Calif.

[21] Appl. No.: 303,575

[22] Filed: Jan. 27, 1989

Related U.S. Application Data

[63] Continuation-in-part of Ser. No. 254,284, Oct. 5, 1988.

[51] Int. Cl.$^5$ .............................. C07C 15/067
[52] U.S. Cl. .................. 585/323; 585/462; 585/466; 585/467
[58] Field of Search ............... 585/466, 467, 323, 462

[56] References Cited

U.S. PATENT DOCUMENTS

| | | | |
|---|---|---|---|
| 3,076,856 | 2/1963 | Carden et al. | 585/323 |
| 3,205,277 | 9/1965 | Pollitzer et al. | 585/323 |
| 3,251,897 | 5/1966 | Wise | 585/455 |
| 3,428,701 | 2/1969 | Ward | 585/323 |
| 3,551,510 | 12/1970 | Pollitzer et al. | 585/323 |
| 3,631,120 | 12/1971 | Eberly et al. | 585/467 |
| 3,751,504 | 8/1973 | Keown et al. | 585/323 |
| 4,026,959 | 5/1977 | Kemme et al. | 585/320 |
| 4,064,068 | 12/1977 | Hasseltine, Jr. | 252/364 |
| 4,415,544 | 11/1983 | Kokotailo et al. | 502/60 |
| 4,440,871 | 4/1984 | Lok et al. | 423/305 |
| 4,567,029 | 1/1986 | Wilson et al. | 502/208 |
| 4,795,847 | 1/1989 | Weitkamp et al. | 585/467 |

FOREIGN PATENT DOCUMENTS

| | | |
|---|---|---|
| 294759 | 12/1965 | Australia . |
| 0012514 | 6/1980 | European Pat. Off. . |
| 0202752A1 | 10/1986 | European Pat. Off. . |
| 0288582 | 10/1987 | European Pat. Off. . |
| 3703291A1 | of 0000 | Fed. Rep. of Germany . |
| 50-010586 | 4/1975 | Japan . |
| 50-011379 | 4/1975 | Japan . |
| 62-226931 | 10/1987 | Japan . |
| 63-14738 | 1/1988 | Japan . |

Primary Examiner—W. J. Shine
Assistant Examiner—E. D. Irzinski
Attorney, Agent, or Firm—E. Thomas Wheelock

[57] ABSTRACT

A process for the selective manufacture of 2,6-diisopropylnaphthalene from naphthalene advantageously combines an equilibration reactor to enhance the amount of monoisopropylnaphthalene fed to the alkylation reactor, and the use of a shape selective catalyst in the alkylation reactor, to obtain an alkylation reaction product in which the 2,6-diisopropylnaphthalene isomer comprises greater than 39 mole percent of the total diisopropylnaphthalene obtained. Further, this combination of reaction steps and conditions produces a reaction product in which the ratio of 2,6-diisopropylnaphthalene to 2,7-diisopropylnaphthalene is greater than 1.0, preferably greater than 1.2. Recycled process components are fed to the equilibration reactor where they are combined with fresh naphthalene feed to provide a monoisopropylnaphthalene enriched feed to the alkylation reactor.

31 Claims, 4 Drawing Sheets

ISOPROPYLATION OF NAPHTHALENE

MONOALKYLATION:

ISOMERIZATION:

DIALKYLATION:

TO THE 2,6 ISOMER:

ISOMERIZATION:

α,β Isomerization

α,α Isomerization

PROCESS FOR SELECTIVE MANUFACTURE OF 2,6-DIISOPROPYLNAPHTHALENES WITH EQUILIBRATION REACTOR

RELATED APPLICATION DATA

This application is a continuation-in-part application of copending application Ser. No. 07/254,284, filed on Oct. 5, 1988.

TECHNICAL FIELD

The present invention relates generally to the manufacture of dialkylnaphthalenes from naphthyl compounds. Specifically, the present invention provides means for substantially improving the process economics of the manufacture of 2,6-diisopropylnaphthalene from naphthalene and propylene by using a non-shape selective catalyst in an equilibration reactor in combination with a shape selective catalyst in an alkylation reactor to provide an alkylation product rich in 2,6-diisopropylnaphthalene.

BACKGROUND OF THE INVENTION

Recently, a new class of engineering thermoplastics has been introduced based upon thermotropic liquid crystal polymers which combines the desirable attributes of moldability with multidirectional mechanical strength superior to conventional thermoplastic materials. Generally, these liquid crystal polymers are polyesters made up of planar, linear disubstituted aromatic compounds, for example, p-hydroxybenzoic acid, p-hydroquinone, 4,4'-dihydroxybiphenyl and 2-hydroxy, 6-naphthenoic acid.

Further commercial opportunities for developing new liquid crystal polymers are largely dependent upon the availability and price of feed stock materials. Certain liquid crystal polymers would be commercially attractive if 2,6-dihydroxynaphthalene or 2,6-dicarboxynaphthalene were readily available. While these feedstocks are not currently readily available, a potentially viable precursor is 2,6-diisopropylnaphthalene, which can be easily converted to the dihydroxy- or dicarboxyforms based upon existing technology. The present invention relates to improvements in the manufacture of 2,6-diisopropylnaphthalene from naphthalene.

Before proceeding with an explanation of these improvements, it is first necessary to establish terminology and a thorough understanding of the isopropylation reaction scheme. The chemical structure which follows shows the positional reference numbers for various substituted naphthalene isomers. Non-hydrogen-bearing carbons are unnumbered because no substitution takes place in these positions.

There are two possible isomers which are formed in the monoisopropylation of naphthalene. Substitution occurs only in the 1 and 2 positions and is respectively denoted $\alpha$ and $\beta$. Any monoisopropyl substitution which takes place in positions 3 through 8 is identical to the $\alpha$ and $\beta$ positions due to their interrelationship in symmetry.

Multiple naphthalene isopropylation is usually denoted by the position number. Some literature references follow the numbering convention just described, while other references discuss the isomers in terms of the a and b terminology. Thus, the 2,6 isomer is the double $\beta$ isomer.

Table 1 describes the statistical distribution of the various diisopropylates using these designations. There is listed no 1,2-, 2,3-, and 1,8-diisopropylnaphthalene for orthodiisopropylation does not occur due to steric effects. In Table 1, it is shown that there are seven disubstituted isomers, of which two (2,6- and 2,7-) are the double $\beta$ product.

TABLE 1

| TYPE | ISOMER | EQUIVALENTS | NORMALIZED FREQUENCY % |
|---|---|---|---|
| $\alpha,\beta$ | 1,6 | 1,6 = 4,7 = 2,5 = 3,8 | 20 |
| | 1,7 | 1,7 = 4,6 = 3,5 = 2,8 | 20 |
| | 1,3 | 1,3 = 2,4 = 5,7 = 6,8 | 20 |
| $\alpha,\alpha$ | 1,4 | 1,4 = 5,8 | 10 |
| | 1,5 | 1,5 = 4,8 | 10 |
| $\beta,\beta$ | 2,6 | 2,6 = 3,7 | 10 |
| | 2,7 | 2,7 = 3,6 | 10 |

Figure 2:
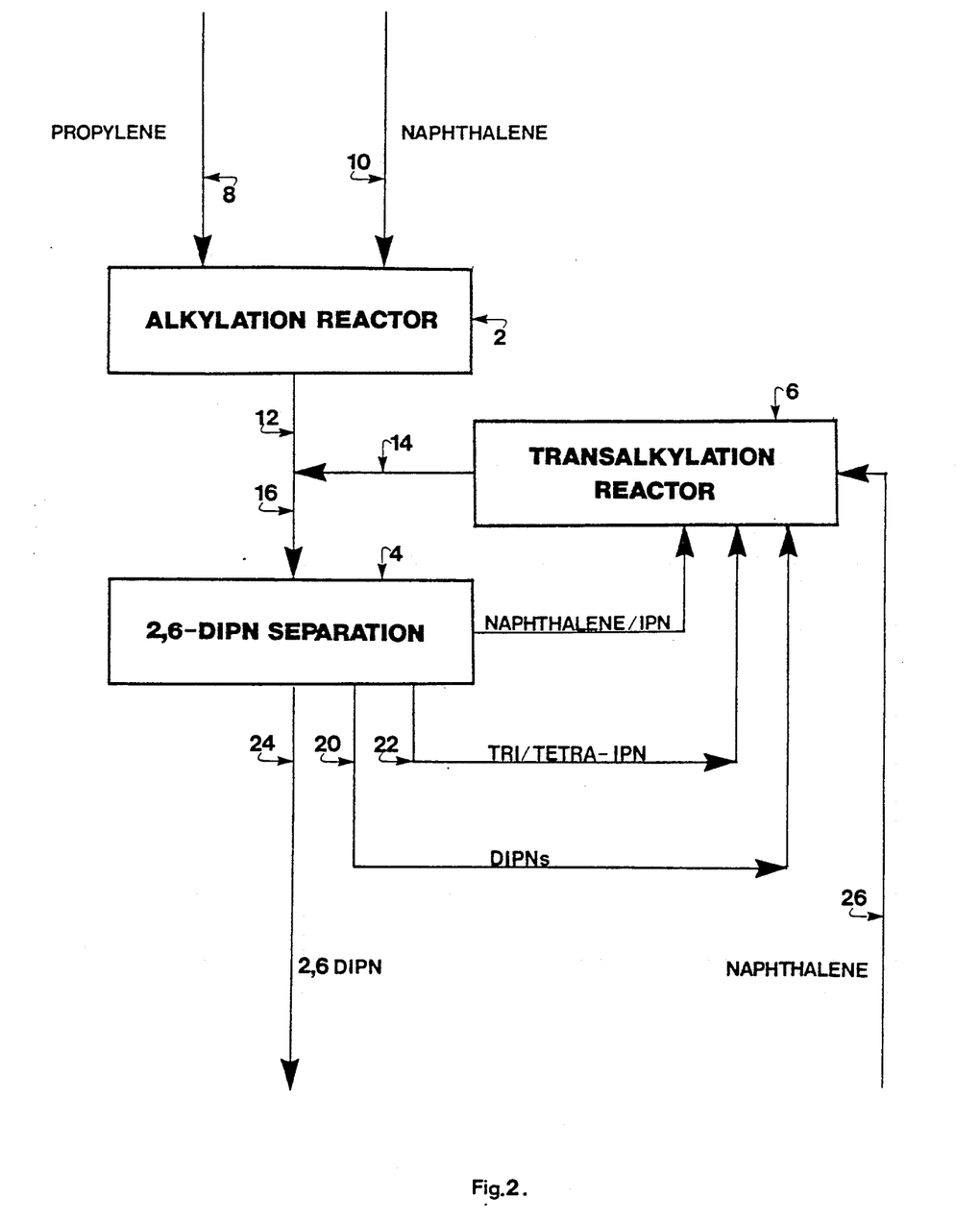
FIG. 2 is a process flow diagram for a prior art process for the manufacture of 2,6-diisopropylnaphthalene.

In the manufacture of diisopropylnaphthalene, it is clear that some monoisopropyl- and triisopropyl products, and a mix of diisopropyl isomers, will also be obtained. In any crude diisopropylnaphthalene product which is not particularly enriched in the desired 2,6-diisopropylnaphthalene isomer, separation of this isomer by thermal distillation is very inefficient and difficult because the boiling points of 2,6-diisopropylnaphthalene and 2,7-diisopropylnaphthalene are very close. Similarly, 2,6-diisopropylnaphthalene isomer separation by fractional crystallization using melting points is inefficient and suffers from yield problems because of the loss of the desired product in the mother liquor, and because of resulting large recycle streams A prior art process for producing 2,6-diisopropylnaphthalene from naphthalene is shown in FIG. 2, labeled "Prior Art." The three main components of this process are alkylation reactor 2, 2,6-diisopropylnaphthalene separation means 4, and transalkylation reactor 6. Propylene feed stream 8 and fresh naphthalene feed stream 10 are contacted in an alkylation reactor 2 containing a solid acid catalyst. Diisopropylnaphthalene product 12 is combined with a transalkylation recycle stream 14 to form stream 16, which is fed to 2,6-diisopropylnaphthalene separation means 4.

2,6-diisopropylnaphthalene separation means 4 can be a combination of unit operations which increase the purity of the desired 2,6-diisopropylnaphthalene product. In one such combination, thermal distillation can be used to separate naphthalene and monoisopropylnaphthalene from the higher boiling polyisopropylnaphthalenes. Thermal distillation can also be used to separate tri- and tetraisopropylnaphthalenes from the diisopropylnaphthalenes. Finally, crystallization or selective adsorption can be used to recover substantially pure 2,6-diisopropylnaphthalene from the other diisopropylnaphthalene isomers. The 2,6-diisopropylene product is represented as stream 24 in FIG. 2. Naphthalene and monoisopropylnaphthalene recycle stream 18, diisopropylnaphthalene recycle stream 20, tri- and tetraisopropylnaphthalenes stream 22 and napthalene feed stream 26 are fed to transalkylation reactor 6 containing a solid acid catalyst. The transalkylation reaction product, transalkylation recycle stream 14, is typically rich in diisopropylnaphthalene and is typically at equilibrium, being characterized by a 2,6/2,7-diisopropylnaphthalene molar ratio of about 1 and a diisopropylnaphthalene fraction containing no greater than 39 mole percent 2,6 diisopropylnaphthalene. Since a non-shape selective catalyst is used in the alkylation reactor, the composition of diisopropylnaphthalene product 12 will be similar to stream 14 and when combined, the feed to 2,6 diisopropylnaphthalene separating means 4 will also have a 2,6/2,7 ratio of about 1 and contain about 39 mole percent 2,6 diisopropylnaphthalene in the diisopropylene fraction.

Even if a shape selective catalyst were used for the alkylation step to produce an alkylate stream 12 with a 2,6/2,7 diisopropylnaphthalene molar ratio greater than 1.0 and a diisopropylnaphthalene fraction containing greater than 39 mole percent 2,6-diisopropylnaphthalene, the beneficial effect of the shape selective alkylation would be greatly diminished by this process configuration. The recycle stream 14 will typically be at equilibrium, with a 2,6/2,7 diisopropylnaphthalene molar ratio about 1.0 and a diisopropylnaphthalene fraction containing about 39 mole percent 2,6 diisopropylnaphthalene. Since the recycle stream is typically much larger than stream 12, when the two streams are combined and fed to separating means 4, this stream 16 will have only marginally enhanced 2,6/2,7 diisopropylnaphthalene molar ratio and 2,6 diisopropylnaphthalene content in the total diisopropylnaphthalene.

Therefore, it is an object of this invention to provide a process for the selective manufacture of 2,6-diisopropylnaphthalene which enables more efficient separation of the desired 2,6-diisopropylnaphthalene from other alkylation reaction products than prior art methods.

It is another object of the present invention to provide an alkylation reaction product which is enriched in both total diisopropylnaphthalenes and in the mole ratio of 2,6-diisopropylnaphthalene to 2,7-diisopropylnaphthalene.

It is still another object of the present invention to provide an integrated process scheme in which essentially all of the fresh naphthalene feed is converted to the desired 2,6-diisopropylnaphthalene product resulting in a high process yield and low raw material cost.

These and further objects of the present invention will become apparent to those of ordinary skill in the art with reference to the figures and detailed description below.

SUMMARY OF THE INVENTION

The present invention provides a process having three major components: an equilibration reactor, an alkylation reactor and 2,6-diisopropylnaphthalene separation means. Fresh naphthalene feed and the recycle stream from the 2,6-diisopropylnaphthalene separation means are fed to the equilibration reactor wherein they are brought to thermodynamic equilibrium over an acid catalyst, thereby obtaining an equilibrated feed stream which is rich in β monoisopropylnaphthalene. The equilibrated stream is fed to the alkylation reactor where it is contacted with a propyl moiety-containing compound, preferably propylene, in the presence of a shape selective catalyst under conditions sufficient to convert the equilibrated feed stream and propyl moiety-containing compound to diisopropylnaphthalene. The alkylation reactor product thereby obtained contains greater than 39 mole percent of 2,6-diisopropylnaphthalene among all diisopropylnaphthalenes and, 2,6-diisopropylnaphthalene and 2,7-diisopropylnaphthalene in a mole ratio greater than 1.0. This diisopropylnaphthalene product from the alkylation reactor, rich in the desired 2,6-isomer, is fed to 2,6-diisopropylnaphthalene separation means to obtain substantially pure 2,6-diisopropylnaphthalene and a recycle stream containing naphthalene, monoisopropylnaphthalene, other diisopropylnaphthalenes, tri- and tetraisopropylnaphthalenes for recycle to the equilibration reactor.

The ease of separation reduces the energy required to recover the 2,6-diisopropylnaphthalene. Moreover, because of the higher concentration of 2,6 diisopropylnaphthalene, some of the separation steps required by the prior art process are not required by the process of the present invention, making the separation means less costly. In addition, the higher concentration of 2,6-diisopropylnaphthalene reduces the recycle of other alkylnaphthalenes, making the reactors smaller and less expensive. The net result is a process with lower capital cost as well as lower utility requirements.

The process described herein specifically teaches the preparation of 2,6-diisopropylnaphthalene. However, this process is immediately extendable to any 2,6-dialkynaphthalene. Examples for the alkyl moiety are selected from the group; methyl, ethyl, propyl and butyl.

This technology is also generally applicable to other compounds related to dialkylnaphthalenes. One example is para, para dialkylbiphenyls. Another example would be for the preparation of para dialkylbenzenes. The possible alkyl groups for these examples are similar to those for dialkylnaphthalenes.

The primary requirement for a process which is suitable for the preparation of a particular isomer is that an alkylation catalyst is available which displays high selectivity to a desired isomer The next criteria which must be met is the ability to separate the desired isomer from the unwanted products. Finally, the unwanted products must be recyclable to a species or group of species which are a suitable feedstock for the desired product. Mixed dialkylates can be immediately excluded from this process scheme since extra separations recycles are required for the complete utilization of the feedstocks.

In distinction to the prior art process, in the present invention all of the naphthalene feed is fed to the transalkylation reactor to maximize the transalkylation of higher alkylates and produce an equivalent stream which is rich in mono-isopropylnaphthalene rather than diisopropylnaphthalene. Alkylation of this equilibrated stream with propylene over a shape selective catalyst produces a stream with an enhanced yield of 2,6-diisopropylnaphthalene and enhanced 2,6/2,7- diisopropylnaphthalene molar ratio. This stream is now fed directly to 2,6-diisopropylnaphthalene separating means without dilution by an equilibrated recycle stream thereby retaining its enhanced yield of 2,6-diisopropylnaphthalene and enhanced 2,6/2,7-diisopropylnaphthalene molar ratio and making separation of the 2,6-diisopropylene isomer from the other diisopropylnaphthalene isomers and higher alkylates simpler and more efficient than in previous process schemes.

DETAILED DESCRIPTION OF THE INVENTION

Figure 1:
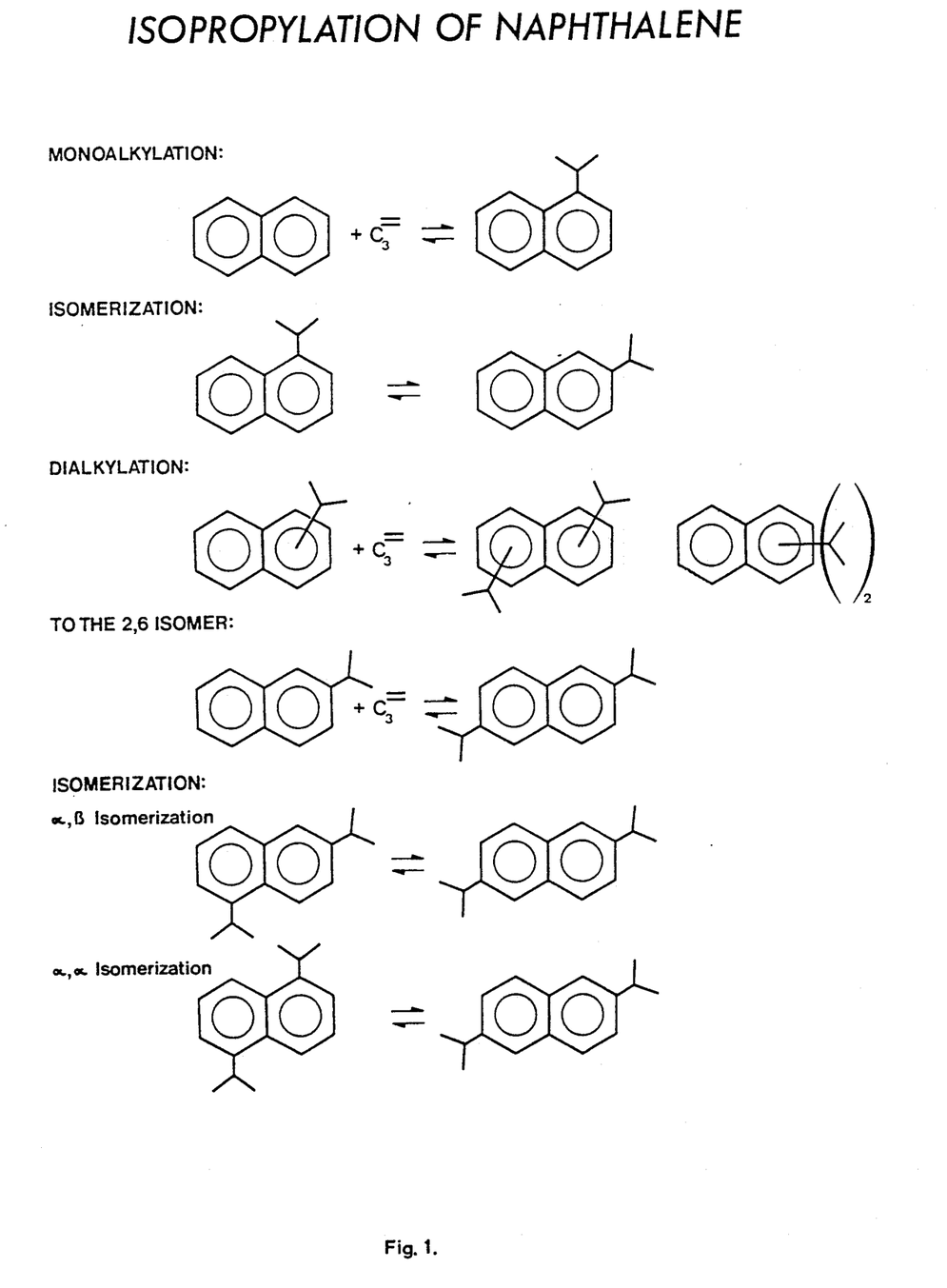
FIG. 1 is a stepwise description of the isopropylation of naphthalene to monoisopropylnaphthalene and diisopropylnaphthalenes.

The isopropylation of naphthalene is known to occur in stepwise manner beginning with monoalkylates, dialkylates, trialkylates, etc. The exact scheme of this progression is set forth more completely in FIG. 1 which also reveals the interconnectivity of the various mono- and di-alkylated species. The different routes and intermediates to the 2,6-diisopropylnaphthalene isomer are of particular interest to the present invention. This isomer can be formed directly by the $\beta$ isopropylation of the monoalkylate or by isomerization of $\alpha,\alpha$ and $\alpha,\beta$ dialkylates.

The equilibrium data for the monoisopropylation of naphthalene is important since the 2,6 isomer is the $\beta,\beta$ product and because the $\beta$ isomer is the preferred thermodynamic species for the monoalkylate. It has been shown by Olah (U.S. Pat. No. 4,288,646) that the concentration of the $\beta$ product increases with the steric bulk of the substituent for monoalkylates of naphthalene. See Table 2. This is predicted to hold true for dialkylates as well.

TABLE 2

| Equilibrium Composition of Mono-Alkylnaphthalene | | |
|---|---|---|
| Alkyl | $\alpha$, % | $\beta$, % |
| Methyl | 24.5 | 75.5 |
| Ethyl | 9.5 | 90.5 |
| Isopropyl | 1.5 | 98.5 |
| tert-Butyl | 0 | 100 |

In the prior art, a considerable number of catalysts have been shown to be effective for the monoisopropylation of naphthalene. (See Table 3.) An equilibrium distribution of products for the monoalkylation has been obtained over zeolite catalysts. (Kemme, U.S. Pat. No. 4,026,959.) It is shown that the concentration of the $\beta$ isomer is a function of the nature of the alkylation catalyst and the reaction operating conditions. It has also been shown that the isomerization of $\alpha$ to $\beta$ was dependent upon temperature, catalyst charge, time and substrate water content.

TABLE 3

| Monoisopropylation of Naphthalene with Propylene over Various Catalysts | | | | | |
|---|---|---|---|---|---|
| Catalyst | Solvent | Reaction Temp °C. | $\alpha + \beta$ Yield | Product Composition % $\alpha$ | $\beta$ |
| Nafion-H | — | 220 | 37 | 10 | 90 |
| HF | heptane | 78 | 91.2 | 3 | 97 |
| H$_3$PO$_4$/Kieselguhr | — | 200 | 36 | 73 | 27 |
| H$_2$SO$_4$ | — | 10 | 90 | 54 | 36 |
| AlCl$_3$ | — | 100 | — | 4 | 96 |
| RE-Y | — | 218 | 93 | — | — |
| BF$_3$ · Et$_2$O | — | ~10 | 69 | 70 | 30 |

Few literature references, however, describe catalysts or conditions for the direct preparation of 2,6-diisopropylnaphthalene. Teijin describes the preparation of the di-$\beta$ product using an AlCl$_3$ catalyst by direct alkylation (Japanese Patent J75011379-B) or via transalkylation (Japanese Patent J75010586-B). Haseltine (U.S. Pat. No. 4,064,068) teaches the equilibrium product composition for about 1.6:1 propylene/naphthalene reaction at 120° C. over excess AlCl$_3$. See Table 4.

TABLE 4

| Equilibrium Composition for Isopropylated Naphthalene | | | | | |
|---|---|---|---|---|---|
| | Naphthalene | Alkylate: Mono | Di | Tri | Other |
| Composition, Weight % | 7 | 26 | 53 | 12 | 2 |
| Composition, Mole % | 11 | 30 | 49 | 10 | 1 |
| Isopropylated Product Composition Mole % | — | 33 | 54 | 11 | 1 |

For the production of 2,6-diisopropylnaphthalene, there are two important measures of the distribution of the diisopropylated species obtained. One is the percentage of 2,6-diisopropylnaphthalene among all diisopropylated naphthalenes. The other is the ratio of the 2,6- to 2,7- isomers. The value of these measures in an equilibrium distribution of diisopropylated naphthalene species was not available in the literature and has been determined using silica-alumina, which is a non-shape selective catalyst (See Example 1). The equilibrium distribution at 225° contains about 39 mole percent 2,6-diisopropylnaphthalene among all the diisopropylnaphthalenes, and a 2,6-/2,7- isomer ratio of 1.0.

In order to achieve selectivities of the desired 2,6-diisopropylnaphthalene higher than the equilibrium yield, it was recognized that it was first necessary to increase the yield of the monoisopropylnaphthalene isomer generally, and then to kinetically increase the production of the 2,6- isomer relative to the 2,7-isomer in the alkylation reactor.

According to the present invention, the use of an equilibration reactor to enrich the proportion of monoisopropylnaphthalene fed to the alkylation reactor in combination with a shape selective alkylation catalyst, provides an enriched diisopropylnaphthalene product which can be more easily and efficiently processed to obtain substantially pure 2,6-diisopropylnaphthalene and a recycle stream for the equilibration reactor.

EXAMPLE 1

To determine the percent 2,6-isomer among all diisopropylnaphthalenes and the 2,6-/2,7- isomer ratio in an equilibrium product distribution, naphthalene was alkylated using a non-shape selective catalyst under conditions such that thermodynamic equilibration of products was obtained.

90.0 grams naphthalene was alkylated using 10.0 grams SiO$_2$-Al$_2$O$_3$ (Grace). Propylene was fed from a heated reservoir at a constant rate of 25 cc/min using a mass flow controller. The temperature of the reaction was 275° C., and the pressure was 50 psig.

TABLE 5

Equilibrium Product Distribution for
Naphthalene Alkylation Using $SiO_2$—$Al_2O_3$

| Naphth. Conv. | mol % Mono | mol % Di | mol % Poly | 2,6/2,7 Ratio | % 2,6 In Di |
|---|---|---|---|---|---|
| 23.4 | 91.9 | 8.1 | 0.0 | 1.00 | 36.8 |
| 94.2 | 31.1 | 51.5 | 17.4 | 1.03 | 38.5 |

The mole percents of mono-, di-, and polyisopropylnaphthalenes obtained at 94.2% conversion agree excellently with the data of Haseltine, see Table 4. This example also demonstrates that the composition of the diisopropylnaphthalenes (mole % 2,6-diisopropylnaphthalene and 2,6-/2,7- ratio) is the same at both high and low naphthalene conversion, showing that equilibrium has been obtained.

The equilibration reactor, according to the present invention, is intended to bring the recycle streams from the 2,6-diisopropylnaphthalene separations section and the fresh naphthalene feed to thermodynamic equilibrium over an acid catalyst. As has already been demonstrated (Table 2), the predominant equilibrium product is β-monoisopropylnaphthalene which is the preferred precursor for the desired 2,6-diisopropylnaphthalene. A variety of equilibration acid catalysts are available, see, for example, the catalysts set forth in Table 3 above. In our preferred embodiment, amorphous silica-alumina is used effectively. The equilibration reactor operating temperature is related to the type of catalyst chosen. Table 3 presents suggested operating temperatures in relation to the catalyst used. In our preferred embodiment, the equilibration reactor, containing an amorphous silica-alumina catalyst is operated at temperatures between 100° C. and 300° C., most preferably in the range 250°-300° C. The equilibration reactor operating pressure should be high enough to prevent significant vaporization of the feed or product components at the reaction temperature. A pressure of 2 to 5 atmospheres is sufficient for this purpose. Another design consideration is to operate the equilibration reactor at a higher pressure than the alkylation reactor to obviate the need for pumping between the two reactors, which will lead to an operating pressure in the range of 1 to 100 atmospheres.

As noted above, the feed to the equilibration reactor comprises fresh naphthalene feed and recycled components from the 2,6-diisopropylnaphthalene separations means. The combined feed stream is desirably adjusted to provide a ratio of moles of propyl groups to moles of naphthyl groups of between 0.2 to 1.8:1, preferably about 1:1. The term propyl groups is used to mean all propyl moieties, including propylene or the propyl groups of the alkylnaphthalenes. The term naphthyl groups is used to mean the sum of naphthalene plus all alkylnaphthalenes. In a commercial plant, this mole ratio will depend on the plant material balance, since the maximum amount of fresh naphthalene that can be added will be equivalent to the 2,6-diisopropylnaphthalene recovered plus any other naphthalene-containing compounds removed from the system, while the recycle stream comprises all of the remaining alkyl naphthalenes plus unconverted naphthalene that are in the alkylation reactor product.

The alkylation reactor design must address an adiabatic temperature rise caused by the exothermic isopropylation reaction. Insufficient heat removal capacity in the alkylation reactor may lead to adverse effects on selectivity and alkylation catalyst life. The alkylation reactor operating temperature ranges between 100° C. and 400° C., preferably between 250° C. and 350° C. The alkylation reactor operating pressure ranges from 1 to 100 atmospheres, preferably 2 to 10 atmospheres, but in any case should be high enough to prevent significant loss of naphthalene and alkyl naphthalenes by vaporization.

The alkylation reaction is conducted under conditions such that the propyl/naphthyl group ratio in the reactor product is between 0.1 and 10, preferably between 1.0 and 2.5. These process conditions lead to a diisopropylnaphthalene product which typically contains greater than 39 mole percent diisopropylnaphthalene and a ratio of 2,6-diisopropylnaphthalene to 2,7-diisopropylnaphthalene greater than 1.0. Under optimum catalyst selection and reaction conditions, a ratio of 2,6-diisopropylnaphthalene to 2,7-diisopropylnaphthalene greater than 1.2 can be achieved.

Before moving on to discuss the specific embodiments of the present invention with reference to the figures, it is important to discuss the use of shape selective catalyst in the alkylation reactor.

The preferred embodiment of the present invention utilizes an acidic crystalline molecular sieve catalyst which has twelve-membered oxygen rings and a pore aperture dimension between 5.5 Å and 7.0 Å. Acidic crystalline molecular sieve structures are obtained by the building of a three dimensional network of $AlO_4$ and $SiO_4$ tetrahedra linked by the sharing of oxygen atoms. The framework thus obtained contains pores, channels and cages or interconnected voids. As trivalent aluminum ions replace tetravalent silicon ions at lattice positions, the network bears a net negative charge, which must be compensated for by counterions (cations). These cations are mobile and may occupy various exchange sites depending on their radius, charge or degree of hydration, for example. They can also be replaced, to various degrees, by exchange with other cations. Because of the need to maintain electrical neutrality, there is a direct 1:1 relationship between the aluminum content of the framework and the number of positive charges provided by the exchange cations. When the exchange cations are protons, the molecular sieve is acidic. The acidity of the sieve is therefore determined by the amount of proton exchanged for other cations with respect to the amount of aluminum.

Crystalline molecular sieve structures are often defined in terms of the number of their tetrahedral units (T atoms). For example, in sodalite the silica and alumina tetrahedra are linked together to form a cubooctahedron, an octahedron truncated perpendicularly to all $C_4$—axes. The sodalite unit is built from four and six membered oxygen rings. The mordenite framework is built from chains of tetrahedra cross linked by oxygen bridges. Each Al or Si tetrahedron is, in addition, part of a five-membered oxygen ring. The chains are then interconnected to obtain the mordenite structure. Mordenite is defined as having twelve-membered oxygen rings. The mordenite pore structure consists of elliptical and noninterconnected channels parallel to the c axis of the orthorhombic structure with pore aperture dimensions of 6.5Å and 7.0Å. A more complete characterization of the zeolites can be found in E. G. Derouane, "Diffusion and Shape-Selective Catalysis in Zeolites," *Intercalation Chemistry*, Ed. by M. Stanley Whittingham (Academic Press, 1982).

ZSM-12 belongs structurally to the mordenite group of zeolites. The pore structure of ZSM-12 consists of linear, non-interpenetrating channels which are formed by twelve-membered rings and possess pore aperture dimensions of 5.5 Å, 5.7 Å and 6.2 Å. See Jacobs, P. A. et al., "Synthesis of High Silica Aluminosilicate Zeolites," *Studies in Surface Science and Catalysis* #33, Elsevier, 1987 page 301. See also, Meier, W. M., "Atlas of Zeolite Structure Types" 2nd ed., Structure Commission of the International Zeolite Association, 1987). Offretite is a 12-oxygen ring zeolite with a pore aperture dimension of 6.7Å and 6.8Å in which the structure also contains a 14-hedron cage.

MeAPSO-46 is also a 12-oxygen ring zeolite with a pore aperture dimension of 6.2Å and 6.4Å.

According to the preferred embodiment of the present invention, acidic crystalline molecular sieve catalysts containing twelve membered oxygen rings are useful in the isopropylation reaction of naphthyl compounds.

Pore structure (dimensions and network) varies greatly among zeolites. Without modifications of the zeolite structure, the lowest pore aperture dimension is about 2.6Å and the highest is 7.4Å. Pores may lead to linear, parallel, or interconnected channels or may give access to larger intracrystalline cavities, sometimes referred to as cages. For all zeolites, the pore opening is determined by the free aperture of the oxygen ring that limits the pore aperture.

The free diameter values given in the channel description and on the ring drawings in the "Atlas of Zeolite Structure Types", (Butterworth's, 1987, 2d Rev. Ed.) are based upon the atomic coordinates of the type species in the hydrated state and an oxygen radius of 1.35Å, as determined from x-ray crystallographic data. Both minimum and maximum values are given for noncircular apertures. In some instances, the corresponding interatomic distance vectors are only approximately coplanar; in other cases the plane of the ring is not normal to the direction of the channel. Close inspection of the framework and ring drawings should provide qualitative evidence of these factors. Some ring openings are defined by a very complex arrangement of oxygen atoms. We have included references to publications which contain extensive drawings and characterization data. The relevant portions of those references are incorporated herein.

Maximum values for the four-, six-, eight-, ten-, and twelve-membered oxygen rings have been calculated to be 2.6 Å, 3.6 Å, 4.2 Å, 6.3 Å and 7.4 Å, respectively.

It should be noted that crystallographic free diameters may depend upon the hydration state of the zeolite, particularly for the more flexible frameworks. It should also be borne in mind that effective free diameters can be temperature dependent. Thus, the free diameters at reaction conditions may differ from those reported above.

As used throughout the instant specification, the term "pore aperture" is intended to refer to both the pore mouth at the external surface of the crystalline structure, and to the intracrystalline channel, exclusive of cages. When a crystalline molecular sieve is hereinafter characterized by a "pore aperture dimension," it is the intent to adopt the geometric dimensional analysis defined as "crystallographic free diameter of channels" in Meier, W. M., Olson, D. H., *Atlas of Zeolite Structure Types*, (Butterworth's, 1987, 2d Rev. Ed.) The term "dimension" is preferred over "diameter" because the latter term implies a circular opening, which is not always accurate in crystalline molecular sieves.

Shape selective reactions occur when the zeolite framework and its pore structure allow substrate molecules of a given size and shape to reach active sites located in the intracrystalline free space, and allow product molecules of a given size and shape to diffuse out of the intracrystalline free space. It is therefore important to characterize accurately the pore structure that is encountered in the various crystalline molecular sieve frameworks.

The nature of interconnecting channels in acidic crystalline molecular sieve catalysts is important in determining their physical and chemical properties. Three types of channel systems have been defined: a one dimensional system, such as found in analcime, does not permit intersection of the channels; two dimensional systems can be found in certain zeolites; and, three dimensional systems have intersecting channels. There are two types of three dimensional channels; in one, the channels are equidimensional, i.e., the pore aperture dimension of all the channels is equal, regardless of the direction. The second type consists of three-dimensional, intersecting channels, but the channels are not equidimensional; the pore aperture dimension depends upon the crystallographic direction. See Donald W. Breck, "Zeolite Molecular Sieves: Structure, Chemistry, and Use," at pp. 59–60 (John Wiley & Sons, 1974).

Crystalline molecular sieves with three-dimensional channels can also contain larger intracrystalline cavities known as cages. These cavities may accommodate substrate molecules and, in principal, play a role in shape selective reactions. For example, sodalite has sodalite cages, as does faujasite. Faujasite is a 12-oxygen ring zeolite with a pore aperture dimension of 7.4 Å and also has supercages (26-hedron) with a cage dimension of 11.8 Å. Wide Type A Zeolite has cages having free dimension of 11.4Å. See E. G. Derouane, "Diffusion and Shape-Selective Catalysis in Zeolites," *Intercalation Chemistry*, at pp. 112–114, Ed. by M. Stanley Whittingham (Academic Press, 1982). See also Thaddeus E. Whyte et al., "Catalytic Materials: Relationship between Structure and Reactivity," at pp. 165–167, *ACS Symposium Series* 248, (American Chemical Society, 1984).

In a particularly preferred embodiment, the acidic crystalline molecular sieve catalyst is synthetic mordenite.

While synthetic mordenite has been described with reference to a particularly preferred embodiment of the present invention, there are other catalysts which can be used in the alkylation reaction to achieve an alkylation product enriched in both total diisopropylnaphthalenes and in the desired 2,6-diisopropylnaphthalene. When mordenite is used, external surface acid site deactivation is preferred. (See below). ZSM-12 can also be used without modification analogous to mordenite. Offretite and MeAPSO-46 also fall into the first class of catalysts whose pore aperture dimensions are between 5.5Å and 7.0Å, prior to any modification to the pores.

However, other catalysts may also be considered which have aperture dimensions in excess of 7.0Å. These other catalysts are obtained by a combination of modifications of commercially available, acidic crystalline molecular sieve products. Zeolite L, zeolite beta, faujasite and SAPO-5, are twelve membered oxygen rings whose pore aperture dimensions typically exceed 7.0Å. SAPO is an acronym for silicoaluminophosphate molecular sieves, first reported in 1984. U.S. Pat. No. 4,440,871 to B. M. Lok et al. MeAPO is an acronym for metal aluminophosphate molecular sieves reported in U.S. Pat. No. 4,567,029 to S. T. Wilson et al. The numbers following the acronym are arbitrary and bear no relationship to structural numbers used previously in the literature, e.g. ZSM-5. For a more complete characterizations of each of the catalyst members discussed above, Reference is made to Flanigen, E. M. et al., *Stud.Surf.Sci.Cat.*, 28, pp. 103–112. See also E. G. Derouane, "Diffusion and Shape-Selective Catalysis in Zeolites," *Intercalation Chemistry*, at pp. 112–114, Ed. by M. Stanley Whittingham (Academic Press, (1987) for a good discussion of ZSM-12.

The preferred Si/Al ratio in Zeolite L is 3.0. The structure of zeolite L consists of columns of symmetrical e-D6R-e units crosslinked to others by single oxygen bridges; planar 12-membered rings produce wide channels parallel to the c-axis. The pore aperture of zeolite L determined by x-ray crystallography was found to be 7.1Å. A more detailed description of the structure of zeolite L can be found in D. W. Breck, John Wiley & Sons, page 113, 1974.

SAPO-5 is structurally analogous to $AlPO_4$-5. $AlPO_4$-5 is a 12-ring sieve with a pore aperture of 7.3Å. A more detailed description of the structure can be found in J. M. Bennett et al., *Intrazeolite Chemistry, ACS Symposium Series* 218, American Chemical Society, page 79, 109, 1983.

Before discussing any modifications to molecular sieves whose pore aperture dimensions exceed 7.0Å, it is first necessary to discuss the concept of shape selective catalysts generally, and the basis for choosing among the below-described modification procedures.

The use of shape selective catalysts to enhance the conversion of substrate to the desired isomer involves the use of a catalyst whose intracrystalline structure permits diffusion of the substrate and the desired isomer under reaction conditions. According to the present invention, certain catalyst modifications have been found to provide a shape selective catalyst particularly beneficial to the conversion of naphthalene and monoisopropylnaphthalene to the desired 2,6-diisopropylnaphthalene product. Among these modifications are dealumination, calcination, and external and internal surface acid site modifications.

The preferred catalysts, mordenite and ZSM-12, as well as offretite and faujasite, can be optimized to yield greater selectivities to the desired 2,6-diisopropylnaphthalene without substantially altering their pore aperture dimensions. One such modification to the preferred catalysts is to dealuminate. Dealumination of acidic crystalline molecular sieve materials can be achieved by exposing the solid catalyst to mineral acids such as HCl. The desired degree of dealumination will dictate the strength of acid used and the time during which the crystalline structure is exposed to the acid. It is also common to use a steam treatment, in combination with the acid leach, to dealuminate zeolite materials. For additional methods of preparing aluminum-deficient zeolites, see J. Scherzer, "The Preparation and Characterization of Aluminum-Deficient Zeolites, " Thaddeus E. Whyte et al., "Catalytic Materials: Relationship between Structure and Reactivity," at pp. 156–160, *ACS Symposium Series* 248, (American Chemical Society, 1984). Dealumination according to the instant invention is intended to achieve a Si/Al ratio between 5 and 100, preferably between 5 and 50. Dealumination can also be applied to the second class of molecular sieve materials whose pore aperture dimensions exceed 7.0Å.

A dealuminated crystalline molecular sieve can be calcined at temperatures between 400° C. and 1000° C., preferably between 400° C. and 600° C. Calcination serves to dehydrate or "heal" Si-OH bonds or "nests" after dealumination. Healing these nests provides a more uniform pore structure within the crystalline material, leading to structural stability and ultimately resulting in improved selectivity.

The calcination conditions of a catalyst can critically affect the catalytic activity. The choice of the calcination gas, for example oxygen or nitrogen, can affect catalyst species differently. In general, calcination temperatures for crystalline molecular sieve catalysts can vary from 300° C. to 1000° C. For a zeolite like H-mordenite, the optimal temperature was found experimentally to lie between 400° C. and 600° C., but preferentially at about 500° C. (Mathur, Kuldeep, Narain, Ph.D. Thesis, University of Pittsburgh, 1977). In the case of H-mordenite, removal of extra and intra crystalline water can be accomplished effectively in presence of an atmosphere of oxygen or nitrogen. This, however, would not be true in the case of organic residues present on the catalyst, as in a surface treated catalyst. In this case, the calcination temperature and the calcination gas are both important in order to minimize the formation of water. In the presence of organic residues, preferably, a nitrogen atmosphere is first used to carbonize the organic residue and release the contained hydrogen as hydrogen gas. Following this step, the atmosphere is changed to oxygen at a temperature sufficient to combust the carbonized residue to $CO_2$, thus minimizing water formation.

Another catalyst treatment (without regard to the pore aperture dimension of the starting material, thereby inclusive of both the classes of catalysts discussed herein), according to the present invention, involves catalyst external surface acid site removal or blockage. The reason for external surface acid removal or blockage is that inactivating the external surface of a zeolite catalyst will increase its shape-selective character, as otherwise the external surface acts as a non-shape selective catalyst. An additional reason for external surface acid site blockage or removal relates to coking on the catalyst surface. Unsaturated compounds such as propylene are able to condense on the acidic function of the catalyst surface producing a substantial amount of coke. See, Studies in Surface Science and Catalysis, 34, p. 143. Coke will also be formed at the catalyst pore mouth over time. This buildup will cause the pores to become less accessible to substrate molecules, and eventually close the pores, rendering these channels inactive.

When using catalysts obtained by the treatment of a crystalline molecular sieve whose pore aperture dimensions are initially above 7.0Å, internal acid site modification is used to reduce the pore aperture dimension to an extent which shows an enhanced 2,6-diisopropylnaphthalene concentration above its equilibrium value. Unfortunately, physical characterization data has not as yet been generated for the pore aperture dimensions of the modified species. Instead, catalysts with reduced pore aperture dimensions are best described with reference to their performance in the isopropylation reaction under consideration. Those crystalline molecular sieves which have been adequately modified by internal acid site treatment will perform in the selective isopropylation of naphthalene to provide a diisopropylnaphthalene which contains at least 39 mole percent of 2,6-diisopropylnaphthalene, and a 2,6-/2,7-diisopropylnaphthalene mole ratio greater than 1.0.

Generally speaking, crystalline molecular sieves may be treated to modify internal acid sites by contact with deactivating reagents selected from the group consisting of the halogen, hydridic and organic derivatives of Groups IIIA, IVA, IVB and VA. Preferred embodiments of the internal acid site deactivating reagents include $B_2H_6$, $SiH_4$ and $PH_3$. For a more complete discussion of the internal acid site modification techniques, see A. Thijs et al., *J. Chem. Soc. Faraday Trans.*, 79, 2821 (1983). See also, J. Philippaerts et al., "The Implantation of Boron-Nitrogen Compounds in Mordenite LP and Their Influence on the Adsorption Properties," *Stud. Surf. Sci. Catal.*, 28, 1986, pp. 305-310. The relevant portions of both references being hereby incorporated herein by reference.

In addition to the use of the above described deactivating reagents, which tend to be non-specific, there is an intermediate level of crystalline molecular sieve modification which can be used to perform "pore mouth engineering." These reagents provide an intermediate level since they are not specific for external acid site, but are not entirely non-specific, leading to substantial internal acid site modification. In selecting an intermediate deactivating reagent, the characteristics and pore aperture dimensions of the starting crystalline molecular sieve must be matched against the molecular dimensions of the deactivating reagent.

It has been shown that chemical vapor deposition of $Si(OCH_3)_4$ on H-mordenite can be successfully used to control the intracrystalline pore aperture without substantially affecting the catalyst's internal surface acidic properties. $Si(OCH_3)_4$ can be deposited irreversibly on zeolite, without entering the intracrystalline res. See Niwa, M. et al., *J. Chem. Soc., Faraday Trans.*, 1, 1984, 80, 3135-3145; Niwa, M. et al., "Modification of H-Mordenite by Vapour-phase Deposition Method," *J. Chem.Soc.Commun.*, 1982, pp. 819-20.

Similarly, chemical vapor deposition of deactivating metal chlorides such as $SiCl_4$, $GeCl_4$, $TiCl_4$ and $SnCl_4$ can be effective to modify pore mouth structures without inactivating internal surface acid sites. These metal molecules, with a range of molecular dimensions, can be selected to be larger than the catalyst pore aperture, thereby preventing substantial diffusion into the internal pore. See Hidalgo, C. V. et al., *Zeolites*, 1984, 4, April, pp. 175-180.

It is also recognized that the deactivating agents can be contacted with the molecular sieve in either solution or vapor phase.

As noted above, it is desireable in any case to deactivate external surface acid sites, without regard to the pore aperture dimensions of the starting crystalline molecular sieve, to prevent non-shape selective reactions on the external surface External surface acid site deactivation can be obtained by either acid site blockage or acid removal. One major limitation of both techniques, however, is that the deactivating agent should be selected to preclude internal surface diffusion. This limitation is easily met by the use of deactivation agents in either liquid or gas phase, whose molecules are too large to fit within even the largest pores of known zeolites. One such molecule is triphenylchlorosilane. See Martens, J. A. et al., *Zeolites*, 1984, 4, Apr., p. 98-100.

In another embodiment of external surface acid site modifications, it is sometimes necessary to fill the intracrystalline pores with a hydrocarbon to obtain an internally protected catalyst. Thereafter, either an aqueous acid or complexing agent, which is insoluble in the hydrocarbon contained within the intracrystalline pore, is contacted with the protected catalyst Once the external surface has been deactivated, then the hydrocarbon is removed from said intracrystalline pores. In EP 86543, a non-polar organic substance is added to the zeolite to fill its pores. Subsequently, a deactivating agent solution (in polar solvent) is introduced to the catalyst. Alkali metal salt solutions, acting as ion exchange atoms to remove the acidic proton associated with aluminum, are described as suitable deactivating agents. See also U.S. Pat. No. 4,415,544 which teaches the use of paraffin wax to seal off the pores prior to surface treatment with hydrogen fluoride, which removes the aluminum. Thus, it is seen that an acidic molecular sieve can achieve shape selectivity by restricting diffusion to catalyst sites within the pore structure and by removing or blocking active sites on the external surface of the catalyst Another advantage from the use of a catalyst that achieves shape selectivity in this manner is that the production of tri- and tetraisopropylnaphthalene is substantially reduced, because these larger molecules are even more selectively denied communication between the bulk liquid phase and the catalytic sites than are the diisopropylnaphthalene isomers other than 2,6-diisopropylnaphthalene. This makes it possible to carry the alkylation reaction to a high degree of conversion to diisopropylnaphthalene without forming large quantities of the higher alkylates. The higher degree of conversion and lower concentration of higher alkylates leads to a higher concentration of diisopropylnaphthalenes in the alkylation reactor product and an easier and more efficient separation of 2,6-diisopropylnaphthalene.

Figure 3:
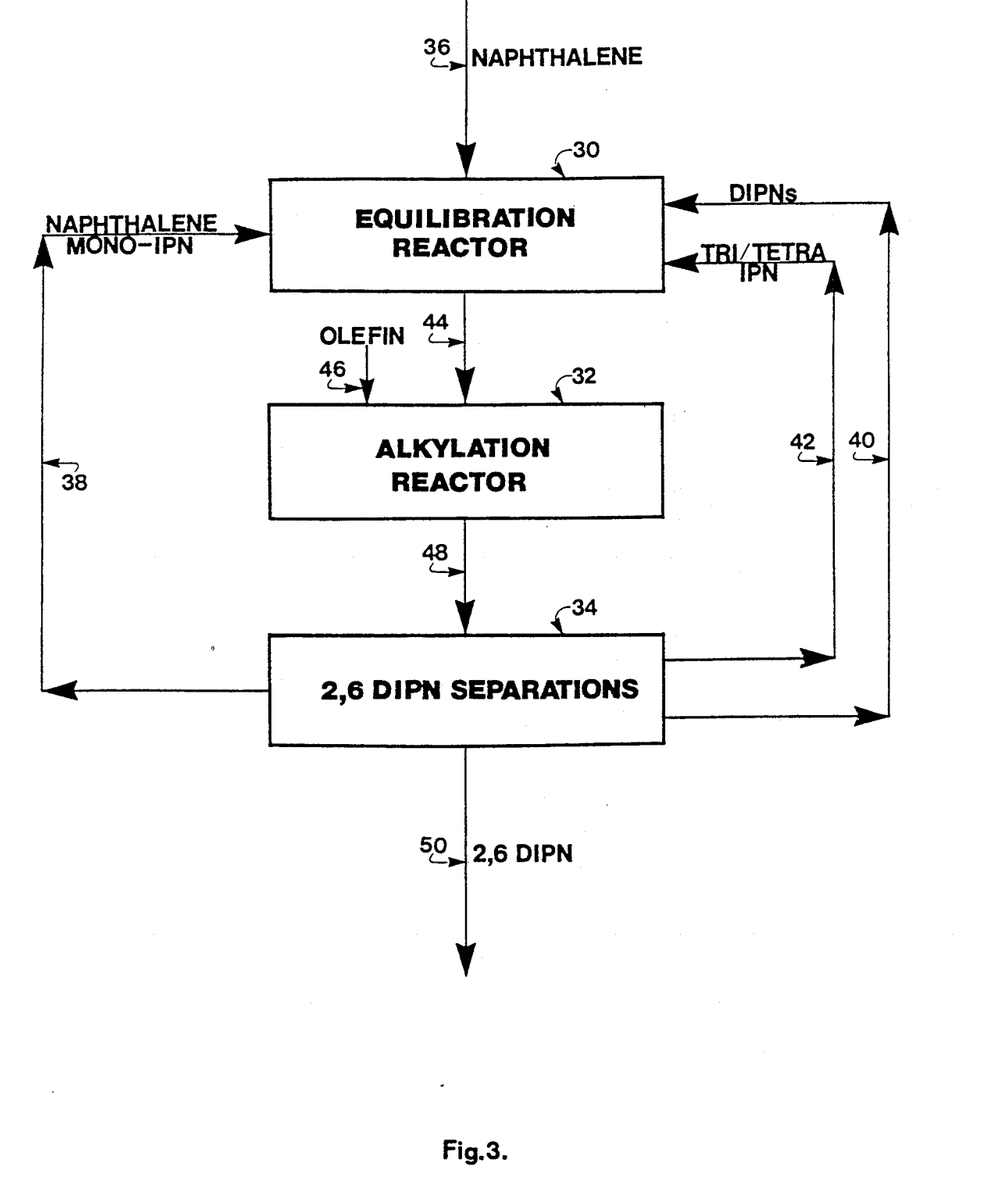
FIG. 3 is a process flow diagram for one embodiment of the present invention.

Referring now to FIG. 3, a preferred embodiment of the present invention is shown. The three main process components are: equilibration reactor 30, alkylation reactor 32 and 2,6-diisopropylnaphthalene separation means 34. Fresh naphthalene feed stream 36 is provided to equilibration reactor 30 where it is combined with naphthalene and monoisopropylnaphthalene recycle stream 38, diisopropylnaphthalene recycle stream 40 and tri- and tetraisopropylnaphthalenes recycle stream 42. This reaction mass is brought to thermodynamic equilibrium over an amorphous silica-alumina catalyst, thereby obtaining an equilibration reaction product which is rich in monoisopropylnaphthalene. Equilibrated feed stream 44 is then fed to alkylation reactor 32 where it is contacted with propylene feed stream 46 in the presence of a shape selective catalyst, chosen to optimize the yield of 2,6-diisopropylnaphthalene. The reaction conditions for both the equilibration reactor 30 and the alkylation reactor 32 were described above.

These process conditions lead to a diisopropylnaphthalene product which typically contains greater then 39 mole percent diisopropylnaphthalene and a ratio of 2,6-diisopropylnaphthalene to 2,7-diisopropylnaphthalene greater than 1.0. Under optimum catalyst selection and reaction conditions, a ratio of 2,6-diisopropylnaphthalene to 2,7-diisopropylnaphthalene greater than 1.2 can be achieved.

2,6-diisopropylnaphthalene enriched stream 48 is then fed to 2,6-diisopropylnaphthalene separation means 34. A variety of separation schemes is possible, according to this embodiment. In the first embodiment, 2,6-diisopropylnaphthalene enriched stream 48 is first thermally distilled to remove unreacted napthalene and monoisopropylnaphthalene for recycle to the equilibration reactor 30 through naphthalene and monoisopropylnaphthalene recycle stream 38. Subsequently, a second thermal distillation can be used to separate diisopropylnaphthalenes from tri- and tetraisopropylnaphthalenes which are also recycled to the equilibration reactor 30 through tri- and tetra- isopropylnaphthalenes recycle stream 42. Thereafter, according to this embodiment, the diisopropylnaphthalenes are fractionally crystallized to obtain diisopropylnaphthalene recycle stream 40 and 2,6-diisopropylnaphthalene product stream 50. According to this embodiment, it may be necessary to add a solvent or an adduct-forming reagent for the fractional crystallization, and then to recover such solvent or adduct-forming reagent before any recycle to the equilibration reactor 30. It is also possible to utilize some type of selective adsorption to recover 2,6-diisopropylnaphthalene from the other diisopropylnaphthalenes.

It is also possible, in a second embodiment of the 2,6-diisopropylnaphthalene separations, to send the 2,6-diisopropylnaphthalene enriched stream 48 directly to fractional crystallization or selective adsorption without removing the naphthalene, monoisopropylnaphthalenes, tri- and tetraisopropylnaphthalenes via thermal distillation. The design and selection of this embodiment are related to the alkylation product composition and the size of the various recycle streams, and both are certainly within the skill of the ordinary artisan.

Figure 4:
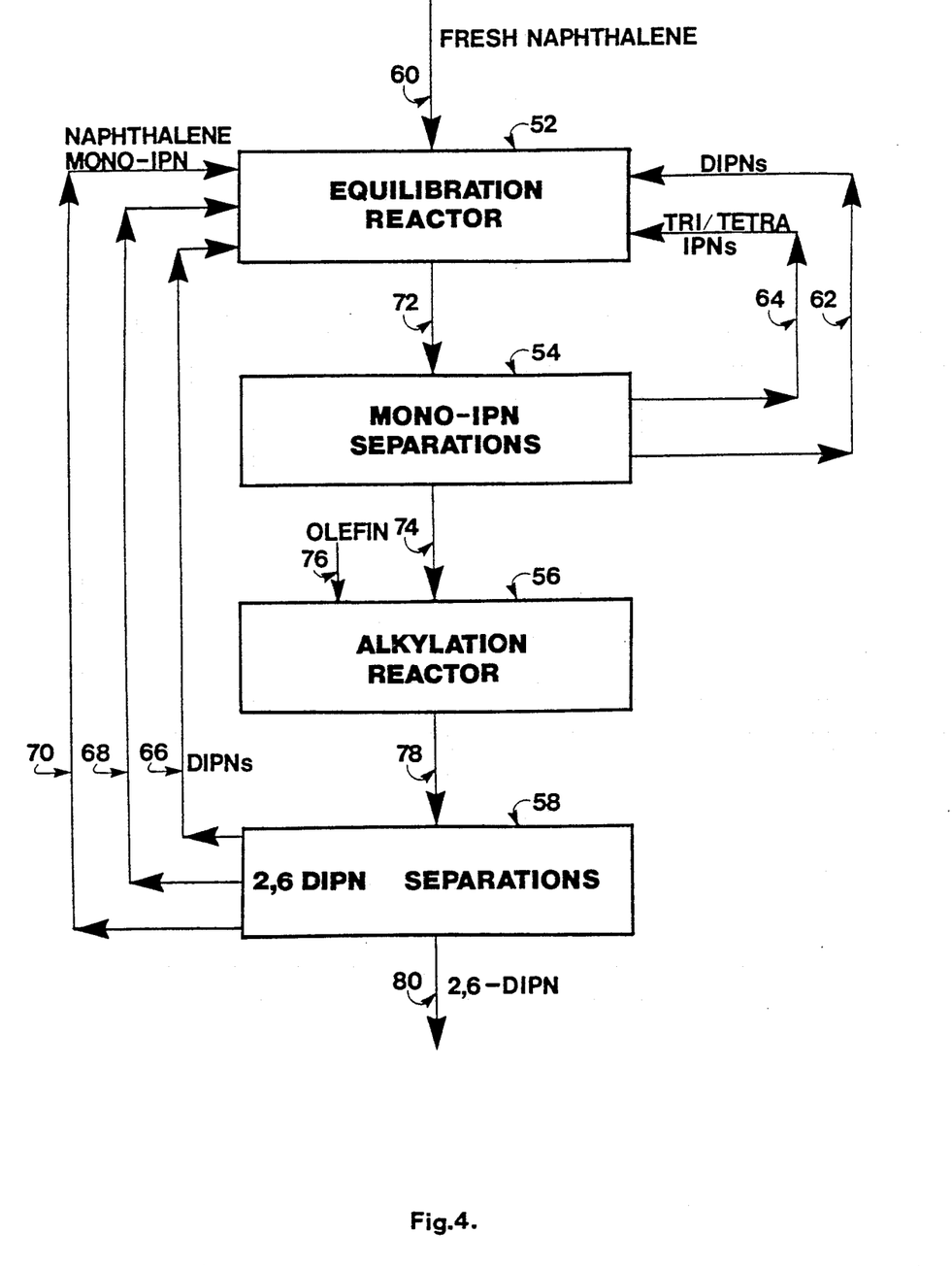
FIG. 4 is a process flow diagram for an alternate embodiment of the present invention.

Another alternative embodiment of the process according to the present invention is set forth in FIG. 4. This process scheme has four major components: equilibration reactor 52, monoisopropylnaphthalene separations means 54, alkylation reactor 56 and 2,6-diisopropylnaphthalene separations means 58. The major difference between this embodiment and the embodiment described with reference to FIG. 3 is the use of monoisopropylnaphthalene separations means 54 to further enhance the concentration of naphthalene and β-monoisopropylnaphthalene in the feed to the alkylation reactor 56. As has been discussed, this is advantageous to the alkylation reaction since a mixture of naphthalene and β-monoisopropylnaphthalene is the preferred substrate for the production of 2,6-diisopropylnaphthalene, a double β isomer.

According to the process depicted in FIG. 4, fresh naphthalene feed 60 is combined with di/tri/tetra isopropylnaphthalenes recycle stream 62, diisopropylnaphthalenes recycle stream 66, tri- and tetraisopropylnaphthalenes recycle stream 68, and naphthalene and monoisopropylnaphthalene recycle stream 70 in the presence of an acid catalyst, preferably amorphous silica-alumina, to obtain an equilibrium reaction mass which is rich in monoisopropylnaphthalene. Equilibrated product stream 72 is fed to monoisopropylnaphthalene separations means 54 wherein thermal distillation is used to separate naphthalene and monoisopropylnaphthalene from diisopropylnaphthalenes, and tri- and tetraisopropylnaphthalenes. The di/tri/tetra isopropylnaphthalene recycle stream 62 is recycled to equilibration reactor 52. Monoisopropylnaphthalene enriched feed stream 74 is then fed to the alkylation reactor 56 where it is contacted with propylene feed stream 76 in the presence of a shape selective catalyst as described above. These process conditions lead to a diisopropylnaphthalene product which typically contains greater than 39 mole percent diisopropylnaphthalene and a ratio of 2,6-diisopropylnaphthalene to 2,7-diisopropylnaphthalene greater than 1.0. Under optimum catalyst selection and reaction conditions, a ratio of 2,6-diisopropylnaphthalene to 2,7-diisopropylnaphthalene greater than 1.2 can be achieved.

Alkylation product stream 78, enriched in the 2,6-diisopropylnaphthalene isomer, is then fed to 2,6-diisopropylnaphthalene separations means 58 wherein substantially pure 2,6-diisopropylnaphthalene is separated from the other alkylation reaction components such as naphthalene, monoisopropylnaphthalene, other diisopropylnaphthalenes, tri and tetraisopropylnaphthalenes. Thus, 2,6-diisopropylnaphthalene product stream 80 is obtained, while diisopropylnaphthalenes recycle stream 66, tri- and tetraisopropylnaphthalenes recycle stream 68, and naphthalene and monoisopropylnaphthalene recycle stream 70 are recycled to the equilibration reactor 52.

As was discussed with reference to the 2,6-diisopropylnaphthalene separation means 34 shown in FIG. 3, there are at least two schemes for separating 2,6-diisopropylnaphthalene from the other process components in the alkylation product stream 78. First, there is an embodiment in which the alkylation product stream 78 is thermally distilled to remove naphthalene and monoisopropylnaphthalenes, and in a second thermal distillation, the higher boiling tri- and tetraisopropylnaphthalenes are removed. Subsequently, the remaining diisopropylnaphthalenes would be subjected to fractional crystallization or reactive adsorption to separate the 2,6-diisopropylnaphthalene isomer from the other diisopropylnaphthalenes.

Alternatively, depending upon the concentration of the desired 2,6-diisopropylnaphthalene in the alkylation product stream 78, this stream may be sent directly to fractional crystallization or selective adsorption for separating the 2,6-diisopropylnaphthalene isomer from the other alkylation reaction components.

Fractional crystallization of diisopropylnaphthalene isomers is performed at temperatures ranging from −20° C. to 0° C.

The following examples illustrate the effectiveness of a shape selective catalyst in producing diisopropylnaphthalene streams that contain higher than the equilibrium concentration of 2,6-diisopropylnaphthalene and have a mole ratio of 2,6/2,7-diisopropylnaphthalene significantly greater than 1.0. Results were determined by gas chromatography.

EXAMPLE 2

The following example illustrates the high selectivity to 2,6-diisopropylnaphthalene attained when alkylating naphthalene over a shape selective catalyst. The catalyst was H-mordenite dealuminated with steam calcining followed by a wash with 0.5N HCl, followed by calcining at 500° C. for 8 hours. The reaction was conducted in a stirred autoclave. Liquid charge was 90 grams, and catalyst charge was 1 gram.

| NAPHTHALENE ALKYLATION OVER A SHAPE-SELECTIVE CATALYST | | |
|---|---|---|
| Temperature, °C. | 275 | 275 |
| Conversion, % | 76.3 | 95.1 |
| Composition, mol % | | |

-continued

| NAPHTHALENE ALKYLATION OVER A SHAPE-SELECTIVE CATALYST | | |
|---|---|---|
| Mono IPN | 55 | 29.1 |
| Di-IPN | 42.9 | 60.3 |
| Tri/Tetra-IPN | 1.74 | 4.71 |
| 2,6 in DIPN | 63.2 | 60.8 |
| 2,6/2,7 Ratio | 2.65 | 2.50 |

This example shows that even at high conversion the 2,6-diisopropylnaphthalene in the diisopropylnaphthalene fraction and the ratio of 2,6 to 2,7 are both substantially higher than the equilibrium values of about 39% and 1.0, respectively. It also shows that the amount of tri- and tetraisopropylnaphthalenes is substantially lower than the equilibrium value.

EXAMPLE 3

In the process for making 2,6-diisopropylnaphthalene it will be necessary for good economics to recycle unreacted naphthalenes and the other alkylnaphthalenes so that they may be largely converted to the desired 2,6-diisopropylnaphthalene. In one embodiment of the process illustrated in FIG. 3, the recycle naphthalene and alkylnaphthalenes are combined with fresh naphthalene to give a ratio of total propyl groups to total naphthyl groups in the range of 0.1 to 2.0 and then equilibrated over a non-shape selective catalyst. To simulate equilibration of this recycle stream, a feed was made up by mixing 374 grams of diisopropylnaphthalene with 226 grams of naphthalene to give a propyl/naphthyl ratio of about 1. To this mixture 30 grams of silica/alumina catalyst was added, and the system was allowed to come to equilibrium at 275° C., with the following results:

| COMPOSITION OF EQUILIBRATION REACTOR PRODUCT | |
|---|---|
| Temperature, °C. | 275 |
| Propyl/Naphthyl mol ratio | 0.93 |
| Composition, mol % | |
| Naphthalene | 29.8 |
| Mono IPN | 46.4 |
| Di-IPN | 20.3 |
| Tri-IPN | 1.4 |
| Tetra-IPN | 0.2 |
| 2,6 in Di-IPN | 39 |
| 2,6 + 2,7 in Di-IPN | 79 |
| 2,6/2,7 ratio | 0.97 |

This illustrates the effectiveness of a silica/alumina catalyst in transalkylating this feed mixture to an equilibrium product rich in naphthalene and monoisopropylnaphthalene.

EXAMPLE 4

The material shown in Example 3 was alkylated with propylene in a stirred autoclave at a pressure of 50 psig and a temperature of 290° C. The catalyst was prepared as described in Example 2. Liquid charge was 90 grams, and catalyst charge was 1 gram. The reaction was followed over time and the analysis of the reaction mixture as follows:

| ALKYLATION OF EQUILIBRATED FEED | | | | |
|---|---|---|---|---|
| | Time, Hours | | | |
| | 2 | 4 | 11 | 23 |
| Product Distribution, mole % | | | | |
| Naphthalene | 15.5 | 8.5 | 2.3 | 0.5 |
| Mono-IPN | 42.4 | 33.7 | 20.8 | 9.7 |
| Di-IPN | 38.0 | 52.4 | 68.8 | 78.7 |
| Tri-IPN | 1.5 | 2.3 | 3.6 | 6.0 |
| Tetra-IPN | 0.6 | 0.9 | 1.5 | 2.9 |
| 2,6 in Di-IPN | 52 | 55 | 56 | 56 |
| 2,6/2,6 Ratio | 1.6 | 1.8 | 1.9 | 1.8 |

This example illustrates that the composition of the diisopropylnaphthalene fraction is much enriched in 2,6-diisopropylnaphthalene and has a high 2,6/2,7 ratio relative to an equilibrium product. Moreover, the concentration of tri- and tetraisopropylnaphthalenes is substantially reduced even at the highest conversion.

EXAMPLE 5

The composition of the alkylated product can be even further enriched in 2,6-diisopropylnaphthalene if the equilibrated feed, such as that shown in Example 3, is distilled to separate the naphthalene and monoisopropylnaphthalene from the higher alkylnaphthalenes, as shown in FIG. 4. The following example illustrates the alkylation of a feed synthesized to represent a distilled, equilibrated feed with a propyl/naphthyl ratio of about 1. The reaction was conducted in a stirred autoclave. Reactor pressure was 50 psig, and the temperature was 290°. The catalyst was prepared as in Example 2. Liquid charge was 90 grams, and catalyst charge was 1 gram.

| ALKYLATION OF DISTILLED EQUILIBRATED FEED | | | | |
|---|---|---|---|---|
| | Time, hours | | | |
| | 0 | 4 | 10.5 | 23 |
| Product Distribution, mole % | | | | |
| Naphthalene | 40.8 | 11.3 | 3.1 | 0.6 |
| Mono-IPN | 56.4 | 42.7 | 26.3 | 14.0 |
| Di-IPN | 0.9 | 42.4 | 64.7 | 76.8 |
| Tri-IPN | 0.0 | 1.3 | 3.1 | 5.3 |
| Tetra-IPN | 0.0 | 0.5 | 0.8 | 1.2 |
| 2,6 in Di-IPN | | | 63 | 63 | 62 |
| 2,2/2,7 Ratio | | | 2.6 | 2.5 | 2.4 |

This example clearly illustrates the high 2,6-diisopropylnaphthalene concentration and high 2,6/2,7 ratio that can be achieved by this process alternative.

EXAMPLE 6

The above examples were all generated in a batch or semi-bath mode. However, a commercial plant would probably be operated at such a scale that continuous operation would be preferred. In order to demonstrate the feasibility of continuous operation, a run was made in a fixed bed reactor 0.75 cm in diameter by 8.7 cm long containing about 4 cc of 60–80 mesh catalyst. The catalyst was prepared as in Example 2, then pressed into tablets, crushed, and screened to size. The feed to the reactor was the same equilibrated feed shown in Example 3. Alkylation conditions were 290° C., 100 psig pressure, and a liquid hourly space velocity of 3 hr$^{-1}$. The results are shown in the following table.

ALKYLATION IN A FIXED BED REACTOR

| | Time, hours | | | | |
|---|---|---|---|---|---|
| | 0 | 51 | 77 | 92 | 125 |
| Product Distribution, mole % | | | | | |
| Naphthalene | 29.8 | 7.1 | 8.1 | 8.5 | 10.0 |
| Mono-IPN | 46.4 | 24.6 | 24.9 | 26.8 | 26.5 |
| Di-IPN | 20.3 | 62.1 | 61.6 | 59.7 | 58.8 |
| Tri-IPN | 1.4 | 3.0 | 2.5 | 2.4 | 2.6 |
| Tetra-IPN | 0.2 | 1.0 | 0.8 | 0.7 | 0.8 |
| 2,6 in di-IPN | 39 | 56 | 57 | 57 | 57 |
| 2,6/2,7 Ratio | 0.97 | 1.9 | 1.9 | 1.9 | 1.9 |

From this example it is seen that the composition of the diisopropylnaphthalene fraction in the reactor product is essentially the same as that obtained via a batch alkylation of the same feed, Example 4. Moreover, there is no indication of a loss in catalytic activity over the 125 hour run period.

We claim:

1. A process for obtaining 2,6-diisopropylnaphthalene which comprises the steps of
   (a) providing an equilibration reactor, an alkylation reactor and means for separating 2,6-diisopropylnaphthalene from a mixture of naphthalene, monoisopropylnaphthalene, other diisoproplylnaphthalenes, triisopropylnaphthalenes and tetraisopropylnaphthalenes;
   (b) providing fresh naphthalene feed, a propyl moiety-containing compound selected from the group comprising propyl chloride, propyl alcohol, and propylene, an acid catalyst, a shape selective acidic catalyst comprising an acidic crystalline molecular sieve having twelve membered oxygen rings and pore aperture widths between 5.5 Å and 7.0 Å; and a recycle stream from said 2,6-diisopropylnaphthalene separation means;
   (c) feeding said fresh naphthalene feed and said recycle stream to said equilibration reactor wherein said fresh naphthalene feed and recycle stream are brought to thermodynamic equilibrium over said acid catalyst thereby obtaining an equilibrated feed stream which is rich in monoisopropylnaphthalene;
   (d) feeding said equilibrated feed stream and propyl moiety-containing compound to said alkylation reactor to obtain a diisopropylnaphthalene product comprising greater than 39 mole percent of 2,6-diisopropylnaphthalene and, 2,6-diisopropylnaphthalene and 2,7-diisopropylnaphthalene in a mole ratio greater than 1.0, wherein said equilibrated feed stream is contacted with said propyl moiety-containing compound in the presence of said shape selective acidic catalyst under conditions sufficient to convert said equilibrated feed stream and propyl moiety-containing compound to a diisopropylnaphthalene product;
   (e) feeding said diisopropylnaphthalene product to said 2,6-diisopropylnaphthalene separations means to obtain substantially pure 2,6-diisopropylnaphthalene product and said recycle stream; and,
   (f) recycling said recycle stream to said equilibration reactor.

2. The process of claim 1 wherein said propyl moiety compound is propylene.

3. The process of claim 1 wherein the ratio of moles of propyl groups to the moles of naphthal groups in the feed to the equilibration reactor, after combining said fresh naphthalene feed and said recycle stream, is about 1.0.

4. The process of claim 1 wherein said acid catalyst comprises amorphous silica-alumina catalyst.

5. The process of claim 1 wherein said acidic crystalline molecular sieve is selected from the group consisting of MeAPSO-46, Offretite, ZSM-12 and synthetic mordenite.

6. The process of claim 5 wherein said acidic crystalline molecular sieve catalyst is prepared by treatment of a crystalline molecular sieve selected from the group consisting of Zeolite L, Zeolite Beta, faujasite, and SAPO-5 to reduce said port aperture dimensions.

7. The process of claim 1 wherein said separation means comprise a first thermal distillation column to remove unreacted naphthalene and monoisopropylnaphthalene from said diisopropylnaphthalene product thereby providing a diisopropylnaphthalene bottom product, a second thermal distillation column to separate high boiling components such as triisopropylnaphthalenes from said diisopropylnaphthalene bottom product to provide a diisopropylnaphthalene concentrate, and a fractional crystallizer having at least one stage to separate 2,6-diisopropylnaphthalene from other diisopropylnaphthalene isomers in said diisopropylnaphthalene concentrate.

8. The process of claim 1 wherein the alkylation reaction adds between 0.5 and 2.0 propyl groups per naphthyl group.

9. The process of claim 1 wherein the reaction temperature in the alkylation reactor is between 250° and 350° C.

10. The process of claim 1 wherein the reaction pressure in the alkylation reactor is between 1 and 100 atmospheres.

11. The process of claim 1 wherein the reaction pressure in the alkylation reactor is between 2 and 10 atmospheres.

12. A process for obtaining 2,6-diisopropylnaphthalene which comprises the steps of:
   (a) providing an equilibration reactor, an alkylation reactor and crystallizer or selective adsorption separation means for separating 2,6-diisopropylnaphthalene from a mixture of naphthalene, monoisopropylnaphthalene, other diisopropylnaphthalenes, triisopropylnaphthalenes and tetraisopropylnaphthalenes;
   (b) providing fresh naphthalene feed, a propyl moiet-containing compound selected from the group comprising propylchloride, propylalcohol, and propylene, an acid catalyst, a shape selective acidic catalyst comprising an acidic crystalline molecular sieve having twelve membered oxygen rings and pore aperture widths between 5.5 Å and 7.0 Å; and a recycle stream from said 2,6-diisopropylnaphthalene crystallizer or selective adsorption separation means;
   (c) feeding said fresh naphthalene feed and said recycle stream to said equilibration reactor wherein said fresh naphthalene feed and recycle stream are brought to thermodynamic equilibrium over said acid catalyst thereby obtaining an equilibrated feed stream which is rich in monoalkylnaphthalene;
   (d) feeding said equilibrated feed stream and propyl moiety-containing compound to said alkylation reactor to obtain a diisopropylnaphthalene product comprising greater than 39 mole percent of 2,6-diisopropylnaphthalene and, 2,6-diisopropylnaphthalene and 2,7-diisopropylnaphthalene in a mole ratio greater than 1.0, wherein said equilibrated feed stream is contacted with said propyl moiety-containing compound in the presence of said shape selective acidic catalyst under conditions sufficient to convert said equilibrated feed stream and propyl moiety-containing compound to a diisopropylnaphthalene product;

e) feeding said diisopropylnaphthalene product to said crystallizer or selective adsorption separations means to obtain substantially pure 2,6-diisopropylnaphthalene and said recycle stream; and, (f) recycling said recycle stream to said equilibration reactor.

13. The process of claim 12 wherein said propyl moiety-containing compound is propylene.

14. The process of claim 12 wherein the ratio of moles of propyl groups to the moles of naphthyl groups in the feed to the equilibration reactor, after combining said fresh naphthalene feed and said recycle stream, is about 1.0.

15. The process of claim 12 wherein said acid catalyst comprises amorphous silica-alumina catalyst.

16. The process of claim 12 wherein said acidic crystalline molecular sieve is selected from the group consisting of MeAPSO-46, Offretite, ZSM-12 and synthetic mordenite.

17. The process of claim 12 wherein said acidic crystalline molecular sieve catalyst is prepared by treatment of a crystalline molecular sieve selected from the group consisting of Zeolite L, Zeolite Beta, faujasite, and SAPO-5 to reduce its port aperture dimensions.

18. The process of claim 12 wherein the alkyation reaction adds between 0.5 and 2.0 propyl groups per naphthyl group.

19. The process of claim 12 wherein the reaction temperature in the alkylation reactor is between 250° and 350° C.

20. The process of claim 12 wherein the reaction pressure in the alkylation reactor is between 1 and 100 atmosphere.

21. The process of claim 12 wherein the reaction pressure in the alkylation reactor is between 2 and 10 atmospheres.

22. A process for obtaining 2,6-diisopropylnaphthalene which comprises the steps of:

(a) providing an equilibration reactor, an alkylation reactor, first separation means for separating naphthalene, monoisopropylnaphthalene and mixtures thereof from diisopropylnaphthalene and higher isopropylnaphthalenes, and second separation means for separating 2,6-diisopropylnaphthalene from a mixture of naphthalene, monoisopropylnaphthalene, other diisopropylnapylnaphthalenes, triisopropylnaphthalenes and tetraisopropylnaphthalenes;

(b) providing fresh naphthalene feed, a propyl moiety containing compound selected from the group comprising propylchloride, propylalcohol, and propylene, an acid catalyst, a shape selective acidic sieve catalyst, comprising an acidic crystalline molecular sieve having twelve membered oxygen rings and pore aperture widths between 5.5 Å and 7.0 Å; a first recycle stream from said first separation means and a second recycle stream from said second, 2,6-diisopropylnaphthalene separation means;

(c) feeding said fresh naphthalene feed, said first recycle stream and said second recycle stream to said equilibration reactor wherein said fresh naphthalene feed and said first and second recycle streams are bought to thermodynamic equilibrium over said acid catalyst thereby obtaining an equilibrated feed stream which is rich in monoalkylnaphthalene;

(d) fractionally, thermally distilling said equilibrated feed stream in the first separation means to obtain an equilibrated feed distillate stream consisting of naphthalene, monoisopropylnaphthalene and mixtures thereof, and a bottoms products comprising separated diisopropylnaphthalenes and higher isopropylnaphthalenes which is recycled to said equilibration reactor as said first recycle stream;

(e) feeding said equilibrated feed distillate stream and propyl moiety-containing compound to said alkylation reactor to obtain a diisopropylnaphthalene product comprising greater than 39 mole percent of 2,6-diisopropylnaphthalene and, 2,6-diisopropylnaphthalene and 2,7-diisopropylnaphthalene in a mole ratio greater than 1.0, wherein said equilibrated feed distillate stream is contacted with said propyl moiety-containing compound in the presence of said shape selective acidic catalyst under conditions sufficient to convert said equilibrated feed distillate stream and propyl moiety-containing compound to a diisopropylnaphthalene product;

(f) feeding said diisopropylnaphthalene product to said second separations means to obtain substantially pure 2,6-diisopropylnaphthalene and said second recycle stream; and, (g) recycling said second recycle stream to said equilibration reactor.

23. The process of claim 22 wherein the propyl moiety-containing compound is propylene.

24. The process of claim 22 wherein the ratio of moles of propyl groups to moles of naphthyl groups in the feed to the equilibration reactor, after combining said fresh naphthalene feed and said recycle stream, is about 1.0.

25. The process of claim 22 wherein said acid catalyst comprises amorphous silica-alumina catalyst.

26. The process of claim 22 wherein said acidic crystalline molecular sieve is selected from the group consisting of MeAPSO-46, Offretite, ZSM-12 and synthetic mordenite.

27. The process of claim 22 wherein said acidic crystalline molecular sieve catalyst is prepared by treatment of a crystalline molecular sieve selected from the group consisting of zeolite L, zeolite beta, faujasite, and SAPO-5 to reduce said pore aperture dimensions.

28. The process of claim 22 wherein the alkylation reaction adds between 0.5 and 2.0 propyl groups per naphthyl group.

29. The process of claim 22 wherein the reaction temperature in the alkylation reactor is between 250° and 350° C.

30. The process of claim 22 wherein the reaction pressure in the alkylation reactor is between 1 and 100 atmospheres.

31. The process of claim 22 wherein the reaction pressure in the alkylation reactor is between 2 and 10 atmospheres.

* * * * *